United States Patent
Manhart et al.

(10) Patent No.: US 12,254,534 B2
(45) Date of Patent: Mar. 18, 2025

(54) MOVEMENT-COMPENSATED IMAGE RECONSTRUCTION FOR AN X-RAY BASED IMAGING METHOD

(71) Applicant: Siemens Healthineers AG, Forchheim (DE)

(72) Inventors: Michael Manhart, Fürth (DE); Alexander Preuhs, Erlangen (DE); Manuela Meier, Nuremberg (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/411,393

(22) Filed: Jan. 12, 2024

(65) Prior Publication Data

US 2024/0242397 A1    Jul. 18, 2024

(30) Foreign Application Priority Data

Jan. 17, 2023 (EP) ...................................... 23151982

(51) Int. Cl.
*G06T 11/00* (2006.01)
*G06T 7/285* (2017.01)

(52) U.S. Cl.
CPC ............ *G06T 11/003* (2013.01); *G06T 7/285* (2017.01); *G06T 2207/10081* (2013.01); *G06T 2207/20081* (2013.01); *G06T 2207/20084* (2013.01)

(58) Field of Classification Search
CPC ................... G06T 11/003; G06T 7/285; G06T 2207/10081; G06T 2207/20081;
(Continued)

(56) References Cited

U.S. PATENT DOCUMENTS

| | | | |
|---|---|---|---|
| 2010/0128955 A1* | 5/2010 | Walimbe | A61B 6/5247 382/132 |
| 2011/0200232 A1* | 8/2011 | Forthmann | A61B 6/466 382/128 |

(Continued)

OTHER PUBLICATIONS

European Search Report for EP App. 23151982.8-1210 mailed Jul. 11, 2023, with English translation.
Mezheritsky et al., "Population-based 3D respiratory motion modelling from convolutional autoencoders for 2D ultrasound-guided radiotherapy", Medical Image Analysis, Oxford University Press, Oxofrd, GB, Bd. 75, Oct. 9, 2021, pp. 1-14.
(Continued)

*Primary Examiner* — Van D Huynh
(74) *Attorney, Agent, or Firm* — Lempia Summerfield Katz LLC (57) ABSTRACT

For creation of a movement-compensated image reconstruction in an x-ray based imaging method an optimal object movement trajectory is determined by application of a trained algorithm to an optimal latent vector and the movement-compensated image reconstruction is created depending on projection images, with the assumption that the object would have moved in accordance with the optimal object movement trajectory while the imaging method was being carried out. The optimal latent vector is determined by a predetermined cost function being minimized using the latent vector as an optimization parameter, wherein for each optimization step with a current latent vector, a current object movement trajectory is determined by application of a trained algorithm to the current latent vector, and a current value of the cost function is computed depending on the plurality of projection images, with the assumption that the object would have moved in accordance with the current object movement trajectory while the imaging method was being carried out.

20 Claims, 2 Drawing Sheets

(58) Field of Classification Search
CPC . G06T 2207/20084; G06T 2207/10076; G06T 7/30; G06T 2211/412; G06T 2211/441; G06T 11/005; A61B 6/5264
See application file for complete search history.

(56) References Cited

U.S. PATENT DOCUMENTS

| | | | | |
|---|---|---|---|---|
| 2017/0156690 | A1* | 6/2017 | Yi | A61B 6/5264 |
| 2020/0250835 | A1* | 8/2020 | Alzaga | A61B 5/1114 |
| 2020/0286264 | A1* | 9/2020 | Kaethner | G06T 11/005 |
| 2021/0339046 | A1* | 11/2021 | Lachaine | A61N 5/1037 |
| 2022/0189013 | A1 | 6/2022 | Manhart | |
| 2022/0222781 | A1* | 7/2022 | Jacob | G06N 3/084 |
| 2022/0329876 | A1* | 10/2022 | Djelouah | G06N 3/088 |
| 2023/0196640 | A1* | 6/2023 | Sunnegaardh | G06T 11/005 382/131 |
| 2023/0353764 | A1* | 11/2023 | Ikonin | G06N 3/045 |
| 2024/0089486 | A1* | 3/2024 | Kim | H04N 19/137 |
| 2024/0161484 | A1* | 5/2024 | Wang | G06N 3/09 |
| 2024/0221247 | A1* | 7/2024 | Shi | G06T 7/50 |

OTHER PUBLICATIONS

Preuhs et al., "Motion Gradients for Epipolar Consistency", Fully 3D, 2019, pp. 1-4.

Preuhs, et al. "Appearance Learning for Image-based Motion Estimation in Tomography" IEEE Transactions on Medical Imaging, vol. 39, No. 11, Nov. 2020, pp. 1-13.

Preuhs, et al. "Fast Epipolar Consistency without the Need for Pseudo Matrix Inverses" Proceedings of the Fifth International Conference on Image Formation in X-Ray Computed Tomography (CT-Meeting, Salt Lake City, USA, May 20, 2018), pp. 202-205, 2018.

Sitzmann et al., "Implicit neural representations with periodic activation functions." arXiv preprint arXiv:2006.09661. 34th Conference on Neural Information Processing Systems (NeurIPS 2020), Vancouver, Canada. pp. 1-35.; 2020.

Wang, et al., "Dynamic 2-D/3-D Rigid Registration Framework Using Point-To-Plane Correspondence Model", IEEE Transactions on Medical Imaging, vol. 36, Issue: 9, Sep. 2017, pp. 1939-1954.

* cited by examiner

MOVEMENT-COMPENSATED IMAGE RECONSTRUCTION FOR AN X-RAY BASED IMAGING METHOD

CROSS REFERENCE TO RELATED APPLICATIONS

This application claims the benefit of EP 23151982.8, filed on Jan. 17, 2023, which is hereby incorporated by reference in its entirety.

FIELD

Embodiments relate to a method for creating a movement-compensated image reconstruction for an x-ray based imaging method, wherein a plurality of projection images of an object created while the imaging method is being carried out is provided.

BACKGROUND

With the aid of x-ray based imaging methods, for example Cone-Beam Computed Tomography (CBCT), brain structures inter alia are able to be assessed during surgical interventions. This helps for example in the differential diagnosis of strokes for assignment to the ischemic or the hemorrhagic category. A major obstacle for a high-quality image evaluation however is the movement of the patient, which falsifies the geometric information used for the reconstruction. This leads to stripe or unsharp artifacts.

Techniques for movement compensation may be employed in order to compensate for the movement retrospectively. To this end a fixed movement trajectory of the patient is estimated. On successful estimation of the fixed movement trajectory a movement-compensated image reconstruction may be created.

In this the movement is compensated for example by optimization of a target function. The input for the target function contains a set of projection images and a set of parameters that define the approximated movement trajectory of the patient. If the projection images are referred to as I and the parameters that define the movement trajectory are referred to as X, then the problem of movement compensation may be resolved as follows by determination of optimum parameters X'

$$X' = \operatorname{argmin}_X c(r(I,X)),$$

where r( ) refers to the image reconstruction on the basis of the projection images and the current estimation of the movement trajectory and c( ) refers to a cost function. The cost function is correlated for example with the movement, so that low values correspond to a smaller movement.

As described in the publication by J. Wang, R. Schaffert, A. Borsdorf, B. Heigl, X. Huang, J. Hornegger, A. Maier: "Dynamic 2-D/3-D fixed registration framework using point-to-plane correspondence model", IEEE Transactions on Medical Imaging, Vol. 36, No. 9, pp. 1939-1954, 2017, the cost function may be based on a 2D/3D image registration for example.

The cost function may also be based on consistency conditions, as described in the publications by A. Preuhs, M. Manhart, A. Maier: "Fast Epipolar Consistency without the Need for Pseudo Matrix Inverses", Proc. 15th International Conference on Image Formation in X-Ray Computed Tomography, pp. 202-205, 2018 and A. Preuhs, M. Manhart, E. Hoppe, M. Kowarschik, A. Maier: "Motion gradients for epipolar consistency", Proc. 15th International Meeting on Fully Three-Dimensional Image Reconstruction in Radiology and Nuclear Medicine, p. 110720D, 2019. In this case the image reconstruction r( ) is not necessary in the above equation.

The cost function may further be based on autofocus approaches, such as described in the publication by A. Preuhs, M. Manhart, P. Roser, E. Hoppe, H. Yixing, M. Psychogios, M. Kowarschik, A. Maier: "Appearance Learning for Image-based Motion Estimation in Tomography", IEEE Transactions on Medical Imaging, pp. 1-10, 2020.

A possible parametrization X is based on rotations and translations. In this case three parameters for the rotation and three parameters for the translation are used for each projection image. If the number of projection images is N, then the number of parameters needed amounts to N*6. For a classical CBCT trajectory, that includes 400-600 projection images for example, the parameter vector X would have 2400-3600 entries. This makes the problem of optimization very computation intensive.

In order to alleviate this problem, splines may be used for movement compensation, as described in the publication by Preuhs et al. from 2020 mentioned above. In this case the movement is parameterized by spline nodes. This allows the complexity of the movement compensation problem to be greatly reduced. Thus, for example an individual direction of the movement may be approximated by 20 spline nodes, that leads to a parameter vector X with only 120 entries. A further advantage of the spline is the inclusion of restrictions. This means that the movement of the patient is usually regular, for example, that is inherently taken into account by splines.

A problem with both parameterizations mentioned is that they make many movement trajectories possible that are not physically sensible. Since the cost function is not convex as a rule, these physically not sensible movement trajectories may lead to the optimization in local minima and prevent the successful convergence. Through this the reliable movement compensation is prevented in part.

BRIEF SUMMARY AND DESCRIPTION

Embodiments increase the reliability of the movement compensation during the image reconstruction for x-ray based imaging methods.

The scope of the present disclosure is defined solely by the claims and is not affected to any degree by the statements within this summary. The present embodiments may obviate one or more of the drawbacks or limitations in the related art. Independent of the grammatical term usage, individuals with male, female or other gender identities are included within the term.

Embodiments are based on the idea of selecting a parameterization of an object movement trajectory in such a way that unrealistic or physically impossible movement configurations are not taken into account in the optimization. The object movement trajectories are parameterized in an abstract latent space by corresponding latent vectors and concrete object movement trajectories are created by the use of a correspondingly trained algorithm.

In accordance with one aspect a method for creation of a movement-compensated image reconstruction in an x-ray based imaging method is specified. In this aspect the following steps i), ii), iii) and iv) are carried out, but not necessarily in this order. In accordance with step i) a plurality of projection images of an object created while the imaging method is being carried out is provided. In accordance with ii) a trained algorithm is provided, for example stored on a memory device, that is trained to allocate an object movement trajectory to a latent vector of a predetermined latent space. In accordance with step iii) an optimal object movement trajectory is determined by application of the trained algorithm to an optimal latent vector, for example an optimal latent vector of the latent space, and the movement-compensated image reconstruction is created as a function of the plurality of projection images, with the assumption that the object would have moved in accordance with the optimal object movement trajectory while the imaging method was being carried out.

In accordance with step iv) the optimal latent vector is determined by a predetermined cost function being minimized as the optimization parameter using the latent vector. For each optimization step with a current latent vector a current object movement trajectory is determined in this case by application of the trained algorithm to the current latent vector. A current value of the cost function is computed depending on the plurality of projection images, with the assumption that the object would have moved in accordance with the current object movement trajectory while the imaging method was being carried out.

Depending on the cost function employed, for each of the optimization steps in this case for example, the current value of the cost function may be computed as a function of the predetermined set of consistency conditions, for example epipolar consistency conditions, relating to the plurality of projection images.

This is the case for example for the use of a cost function as in the publications by Preuhs et al. from 2018 and 2019 described at the outset.

As an alternative, for each of the optimization steps for example, a current image reconstruction is created depending on the plurality of projection images, with the assumption that the object would have moved in accordance with the current object movement trajectory while the imaging method was being carried out. The current value of the cost function is then computed as a function of the current image reconstruction.

This is the case for example with the use of cost functions as described in the publication by Wang et al. described at the outset or in the publication by Preuhs et al. from 2020 described at the outset.

The method for creation of a movement-compensated image reconstruction may be a purely computer-implemented method in which all steps of the computer-implemented method are carried out by a data processing facility, that has at least one processing unit. For example, the at least one processing unit is configured or adapted for carrying out the steps of the computer-implemented method. The at least one processing unit or a memory device of the at least one processing unit may store a computer program for example, that contains instructions that, when the at least one processing unit executes the program, cause the at least one processing unit to carry out the computer-implemented method.

In other embodiments the method is not purely computer-implemented, for example when the step of carrying out the imaging method, i.e. for example the creation of the projection images, is part of the method.

The x-ray based imaging method may for example be a computed tomography method, for example a cone-beam computed tomography method. The projection images for example correspond to x-ray radiation detected by an x-ray detector, that passes through the object and is attenuated accordingly. The creation of an image reconstruction based on such projection images then for example includes the determination of corresponding attenuation values in the associated spatial regions of the object.

For image reconstruction various known methods may be used. For example, a geometrical operation may be assigned to each of the projection images for reconstruction, by which the image reconstruction or a part of the image reconstruction is created from the respective projection image. Carrying out a movement compensation in such image reconstructions is likewise known, in order to compensate for movements of the object, for example fixed movements of the object during the recording of the projection images. The operations allocated to the individual projection images are corrected according to the respective estimated or assumed object movement trajectory or the respective corresponding translation and rotation position of the object during the creation of the corresponding projection image.

This correction may be undertaken for example by corresponding rotations and/or translations, that are present in accordance with the object movement trajectory at the corresponding point in time of the creation of the projection image. In other words, an object movement trajectory may be defined by a number of successive rotation operations and/or translation operations. The format in which an object movement trajectory is specified or stored may be different in this case. Corresponding translation vectors and rotation matrixes may be specified or corresponding angles of rotation and translation values and so forth. In order to define a translation and rotation for a given projection image, i.e., an associated step of the object movement trajectory, in general three rotation parameters and three translation parameters are accordingly necessary. The object movement trajectory therefore includes these three rotation parameters and translation parameters directly or in indirect form for each projection image.

The latent vector may be understood for example as a tuple with N entries. The entries may correspond to real or complex numbers. The individual entries of the latent vector do not in general have any obvious meaning. The trained algorithm is trained, from any given latent vector of the latent space, to compute precisely one object movement trajectory, i.e., a sequence of rotation and/or translation operations for each of the projection images or a sequence of the corresponding rotation parameters and translation parameters for the individual projection images.

The size of N may be adapted to the required precision and to the available computing resources. Typically, latent spaces with 50 to 150 dimensions, i.e., accordingly latent vectors with 50 to 150 entries, may be used. What is achieved in this way is that a sufficient modification of the latent vectors is possible to be able to encode complex objects such as the object movement trajectory. The latent space may for example be $\mathbb{R}^N$ or $\mathbb{C}^N$.

It is known that complex inputs, such as texts, images and so forth may be encoded uniquely into a latent space by employing algorithms trained by machine learning. Use of artificial neural networks for this purpose is known for example by what are known as autoencoder networks or variational autoencoder networks. Unless stated otherwise, the term autoencoder may be understood below in such a way that it includes autoencoders in the narrower sense as well as variational autoencoders. Instead of autoencoder networks the term Generative Adversarial Networks (GAN) may also be used.

Such algorithms may be trained in a self-supervised way, so that the algorithms may create precisely one latent vector from a complex input and may reconstruct the input from the same latent vector. Once the algorithm is trained, the reconstructive part of the algorithm, also referred to as a generator module or decoder module depending on the embodiment, may be isolated and used for creation of the reconstructed input based on any given latent vectors.

This concept is used in accordance for creation of object movement trajectories from latent vectors. The trained algorithm has thus been trained, for example on the basis of exclusively physically possible training object movement trajectories, so that, after the training of each such training object movement trajectory, it may be allocated to precisely one latent vector and may reliably and accurately reconstruct the training object movement trajectory from this latent vector. In order to provide that only physically possible training object movement trajectories are used as a basis and accordingly that the reconstruction of any given latent vector is likewise physically possible, the training object movement trajectories may for example be obtained from the actual movement of patients.

For the method for creation of the movement-compensated image reconstruction only the reconstructive portion is needed. There is any given number of latent vectors on which the trained algorithm is based as current latent vectors during the optimization in the predetermined latent space. Accordingly, the result is also any given number of current object movement trajectories, but always those that are physically possible.

Through the reconstruction and evaluation of the cost function the latent vector that minimizes the cost function is identified as the optimal latent vector. The cost function is correlated in this case, as described at the outset, with the actual object movement, so that low values of the cost function correspond to a small amount of movement. Accordingly, the object movement trajectory that corresponds to a smallest possible realistic, since small, movement of the object while the x-ray based imaging method is being carried out is identified as the optimal object movement trajectory.

Merely for clarification it should be mentioned that the use of the latent vector as optimization parameter may be understood in such a way that different current latent vectors are selected from the latent space for different optimization steps in order to carry out the corresponding optimization step. Different known optimization methods may likewise be used as the optimization method.

Target functions are generally referred to in optimization problems, regardless of whether these are to be minimized or to be maximized. When the target function(s) is (are) to be minimized, this involves a cost function. The minimization does not represent any kind of restriction in the present case, since even in the case of a target function to be maximized, a modified target function may always be defined, that is to be minimized.

In the method for creation of a movement-compensated image reconstruction use is made of the knowledge that the movement compensation problem involves a non-convex problem, in that local minima may be problematic in the optimization when these correspond to movement configurations that are not sensible physically. The optimization remaining stuck to a certain extent in local minima and instead the result being an optimal object movement trajectory with merely physically possible or realistic movement configurations may be prevented by the parameterization based on the latent vectors. This enables the reliability of the image reconstruction to be greatly enhanced.

In accordance with at least one embodiment of the method the trained algorithm is configured to allocate to a latent vector of the latent space, for example to each given latent vector of the latent space, a time series of rotations and translations in three-dimensional space as object movement trajectory.

Each rotation may be defined for example by three rotation parameters, for example three angles of rotation, and each translation by three translation values, i.e., displacements in three different spatial directions. The time series of rotations and translations may be a six-dimensional time series for the three rotation and three translation parameters or may also contain six individual time series for the individual degree of freedom or for the rotation and translation parameters. The time series of rotations and translations may also be a time series of rotation matrixes and translation vectors.

For example, the plurality of projection images may contain K projection images. Each projection image corresponds to one of K consecutive recording periods and the time series contains K rotations and K translations.

K in this case is a whole number greater than 1 and may for example lie in the range of 100 to 1,000. For CBCT for example the number of projection images may lie in such a range, for example in the range of 300 to 600.

Thus, during each recording period, one of the K projection images for example is created. Each projection image is thus assigned a rotation and a translation in three dimensions in each case. With this assignment, as described above, the geometrical operation for image reconstruction may be corrected for the corresponding projection image in order to realize the movement compensation.

In accordance with at least one embodiment a plurality of training object movement trajectories is created for creating the trained algorithm, that each describe an actual movement of a test object. For each of the training object movement trajectories a training vector in the latent space is created, for example by use of a coded neural network on the respective training object movement trajectory. A reconstructive neural network is applied to the training vector in order to create a reconstructed object movement trajectory.

At least one predefined loss function is evaluated based on the reconstructed object movement trajectory, where necessary using one or more further neural networks. Network parameters, for example weighting factors and/or bias factors, of the reconstructive neural network, for example of the reconstructive neural network and of the encoding neural network and, where necessary of the one or of the number of further neuronal networks, are configured depending on a result of the evaluation of the at least one loss function.

The encoding neural network may for example be an encoder module of an autoencoder and the reconstructive neural network may be a decoder module of the autoencoder. In the case of a GAN the reconstructive neural network may be a generator module of the GAN and the encoding neural network may be a neural network provided in addition to the GAN. The at least one further neural network may then be a discriminator module of the GAN.

In accordance with at least one embodiment the trained algorithm is configured as a generator module of a GAN network.

GAN networks have proven to be reliable tools for encoding complex input data in latent spaces and for making reliable reconstructions of the input data possible.

A GAN network initially includes the generator module as well as a corresponding discriminator module. The discriminator module however is no longer needed once training has been completed.

In accordance with at least one embodiment, in which the trained algorithm is embodied as a generator module of the GAN network, for creation of the trained algorithm, i.e., for example for training of the algorithm, the plurality of training object movement trajectories is created, that each describe an actual movement of a test object. For each of the training object movement trajectories a training vector is created in the latent space, by an artificial neural network embodied as an encoder being applied to the respective training object movement trajectory. The generator module and the discriminator module of the GAN network are trained using the training vectors as input data.

The GAN network, for example of the generator module and the discriminator module, may be trained in the known way. In this case the generator module, based on the respective training vector, creates a reconstructed object movement trajectory and the discriminator module decides whether the reconstructed object movement trajectory involves such a reconstructed object movement trajectory, also referred to as a fake sample, or a true training object movement trajectory, also referred to as a real sample. The training is carried out until such time as the discriminator module may no longer distinguish true training object movement trajectories from reconstructed object movement trajectories. Now the generator module may be used for reliable creation of object movement trajectories on the basis of any given latent vectors in the latent space.

For example, a known generator loss function and a known discriminator loss function may be employed in order to train the generator module and the discriminator module accordingly. The encoder module may be pre-trained, i.e., may be a known encoding encoder module or may be trained before the training of the GAN network or together with the GAN network.

The encoder module, that creates the respective training vector, is not part of the GAN network in the narrower sense. Instead, GAN networks may be trained on any given inputs, for example noise vectors. In the present case however, they are explicitly created based on actual training object movement trajectories, that represent physically realistic movement constellations, so that conversely the object movement trajectories also created by the generator module represent physically realistic movement constellations. The encoder module, like the discriminator module, is no longer needed once the training has been completed.

In accordance with at least one form of embodiment the trained algorithm is embodied as a decoder module of an autoencoder.

Autoencoders include an encoder module, that may convert a corresponding input, here for example a training object movement trajectory, into a latent vector, and a decoder module, that may reconstruct the input based on the latent vector. The encoder module is also no longer needed after training has been completed.

Autoencoders have proved to be reliable tools for encoding complex input data in latent spaces and for making reliable reconstructions of the input data possible. Above and beyond this autoencoders have the advantage that regularization during the training is not a problem compared with other networks.

The plurality of training object movement trajectories, that each describe an actual movement of a test object, may also be created for creating or training of the autoencoder. For each of the training object movement trajectories a training vector is created in the latent space, by the encoder module of the autoencoder or variational autoencoders being applied to the respective training object movement trajectory. By the decoder module, based on the training vector, a reconstructed object movement trajectory is created, and a loss function is evaluated based on a deviation of the reconstructed object movement trajectory from the training object movement trajectory. Network parameters of the autoencoder, for example of the encoder module and of the decoder module, are adapted depending on a result of the evaluation of the loss function.

Known methods and known loss functions may be employed to adapt the network parameters.

In the present example the encoder module is explicitly trained based on actual training object movement trajectories, that represent physically realistic movement constellations, in order to create the training vectors, so that conversely object movement trajectories created by the decoder module also correspond to physically realistic movement constellations.

In accordance with at least one embodiment, for each of the training object movement trajectories for creation of the respective training object movement trajectory, the test object is monitored during a corresponding test period by at least one camera and the respective training object movement trajectory is determined based on camera images created by the at least one camera during the monitoring.

For example, a position and/or orientation of the test object in a reference coordinate system based on the camera images may be determined and a corresponding sequence of rotations and translations or corresponding rotations and translation parameters may be computed.

In accordance with at least one embodiment at least one visual marker is attached to the test object and the respective training object movement trajectory is determined based on the corresponding positions of the at least one visual marker in the camera images.

The position and/or orientation in the reference coordinate system may for example be determined from the positions in the camera images, since the positions and orientations of the at least one camera in the reference coordinate system are known.

In this way a reliable recording of exclusively physically realistic movement constellations may be achieved and accordingly the reliability of the trained algorithm and accordingly of the entire method may be enhanced.

The object may, for example, involve a head of a patient. In the x-ray based imaging of the head the movement compensation described is able to be carried out with especially high accuracy, since the assumption of fixed movements, for example without deformation of the object, is fulfilled especially well.

In accordance with a further aspect, a method for x-ray based imaging is also specified. In this method a plurality of projection images of an object is created and a method for creation of a movement-compensated image reconstruction is carried out in accordance based on the plurality of projection images.

The method for x-ray based imaging is for example a cone-beam computed tomography method.

For application cases or application situations that may arise with the method, and that are not explicitly described here, there may be provision that, in accordance with the method, an error message and/or a request for input of a user confirmation is output and/or a default setting and/or a predefined initial state is set.

In accordance with a further aspect, a data processing facility is specified, that includes at least one processing unit. The at least one processing unit is configured or adapted for carrying out a method for creation of a movement-compensated image reconstruction.

In accordance with a further aspect, an apparatus for x-ray based imaging is specified. The apparatus includes an x-ray imaging modality, that is configured to create a plurality of projection images of an object. The apparatus includes a memory device, that stores a trained algorithm, that is trained to allocate an object movement trajectory to a latent vector of a predetermined latent space. The apparatus includes at least one processing unit, that is configured to determine an optimal object movement trajectory by application of the trained algorithm to an optimal latent vector and to create the movement-compensated image reconstruction depending on the plurality of projection images, with the assumption that the object would have moved in accordance with the optimal object movement trajectory while the imaging method was being carried out.

The at least one processing unit is configured to minimize a predetermined cost function using the latent vector as an optimization parameter, in order to determine the optimal latent vector and, in doing so, to determine a current object movement trajectory for each optimization step with a current latent vector by application of the trained algorithm to the current latent vector, and to compute a current value of the cost function depending on the plurality of projection images, with the assumption that the object would have moved in accordance with the current object movement trajectory while the imaging method was being carried out.

A processing unit may for example be understood as a data processing device that contains a processing circuit. The processing unit may, for example, process data for carrying out computing operations. Where necessary this also includes operations for carrying out indexed accesses to a data structure, for example a look-up table (LUT).

The processing unit may for example contain one or more computers, one of or more microcontrollers and/or one or more integrated circuits, for example one or more Application-Specific Integrated Circuits (ASIC), one or more Field-Programmable Gate Arrays (FPGA), and/or one or more systems on a chip (SoC). The processing unit may also contain one or more processors, for example one or more microprocessors, one or more central processing units (CPU), one or more Graphics Processor Units (GPU) and/or one or more signal processors, for example one or more Digital Signal Processors (DSP). The processing unit may also contain a physical or a virtual network of computers or others of the units.

In different embodiments the processing unit contains one or more hardware and/or software interfaces and/or one or more memory units.

A memory unit may be configured as volatile data memory, for example as dynamic random access memory (DRAM) or static random access memory (SRAM), or as non-volatile data memory, for example as read-only memory (ROM), as programmable read-only memory (PROM), as erasable programmable read-only memory (EPROM), as electrically erasable programmable read-only memory (EEPROM), as flash memory or Flash EEPROM, as ferroelectric random access memory (FRAM), as magneto resistive random access memory (MRAM) or as phase-change random access memory (PCRAM).

Further forms of embodiment of the apparatus follow directly from the various embodiments of the method and vice versa. For example, individual features and corresponding explanations as well as advantages relating to the different forms of embodiment may be transferred to forms of embodiment of the apparatus. For example, the apparatus is configured or programmed for carrying out the method. For example, the apparatus carries out a method.

In accordance with a further aspect, a first computer program with first instructions is specified. When the first instructions are executed by a data processing facility, for example a data processing facility, the first instructions cause the data processing facility to carry out a method for creation of a movement-compensated image reconstruction.

In accordance with a further aspect, a second computer program with second instructions is specified. When the second instructions are executed by a data processing facility, for example an apparatus for x-ray based imaging, for example by the at least one processing unit of the apparatus, the second instructions cause the apparatus to carry out a method for creation of a movement-compensated image reconstruction and/or a method for x-ray based imaging.

In accordance with a further aspect, a computer-readable memory medium is specified, that stores a first computer program and/or a second computer program in accordance with the embodiments described herein.

The first computer program, the second computer program and also the computer-readable memory medium may be expressed as respective computer program products having the first and/or the second instructions.

Embodiments are further explained in greater detail below with the aid of embodiments and associated schematic diagrams. In the figures the elements or elements with the same function may be labeled with the same reference characters. The description of similar elements or elements with the same function may where necessary, not be repeated in relation to different figures.

DETAILED DESCRIPTION

Figure 1:
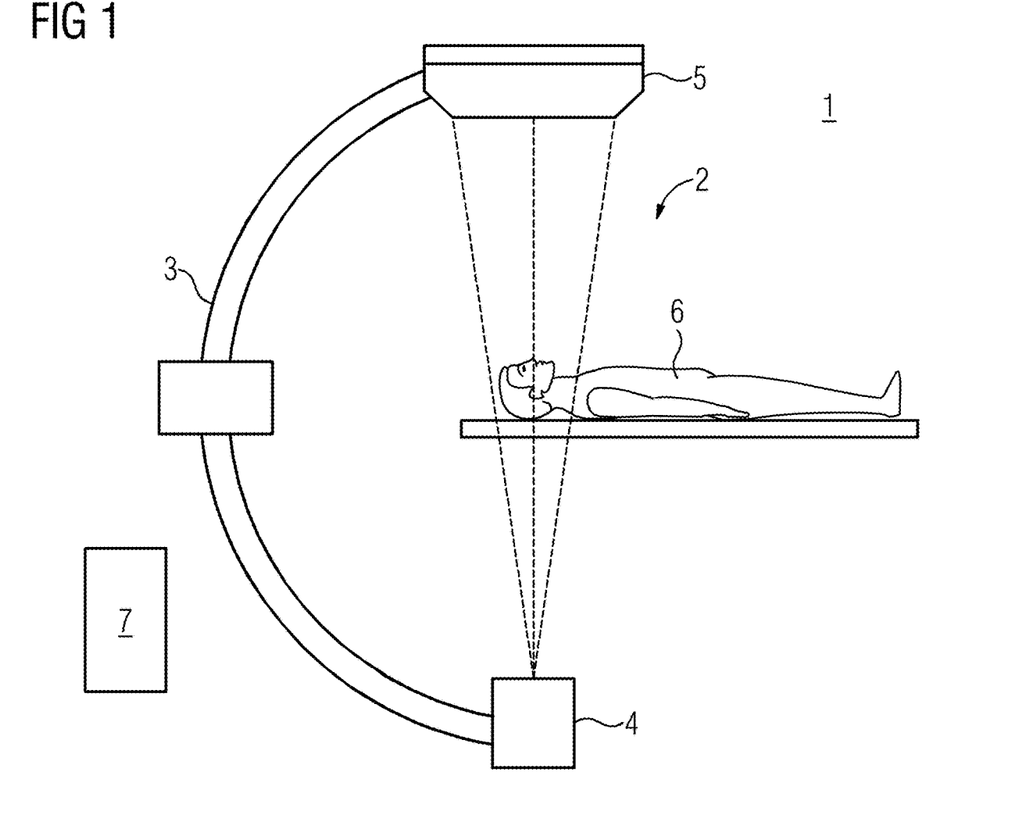
FIG. 1 depicts a schematic diagram of an example of an embodiment of an apparatus for x-ray based imaging.

Shown schematically in FIG. 1 is an apparatus 1 for x-ray based imaging including an x-ray imaging modality 2. The x-ray imaging modality 2 is shown by way of example as a device for cone-beam computed tomography, CBCT, and includes for example a C-arm 3 with an x-ray source 4 and an x-ray detector 5 arranged opposite it. Arranged between x-ray source 4 and x-ray detector 5 is an object 6, for example the head of a patient. The apparatus 1 includes a processing unit 7. The apparatus 1, for example the processing unit 7, includes a memory device (not shown), that stores a trained algorithm 12 (see FIG. 3, FIG. 4), that is trained to allocate an object movement trajectory to a latent vector of a predetermined latent space (see FIG. 3, FIG. 4).

Figure 4:
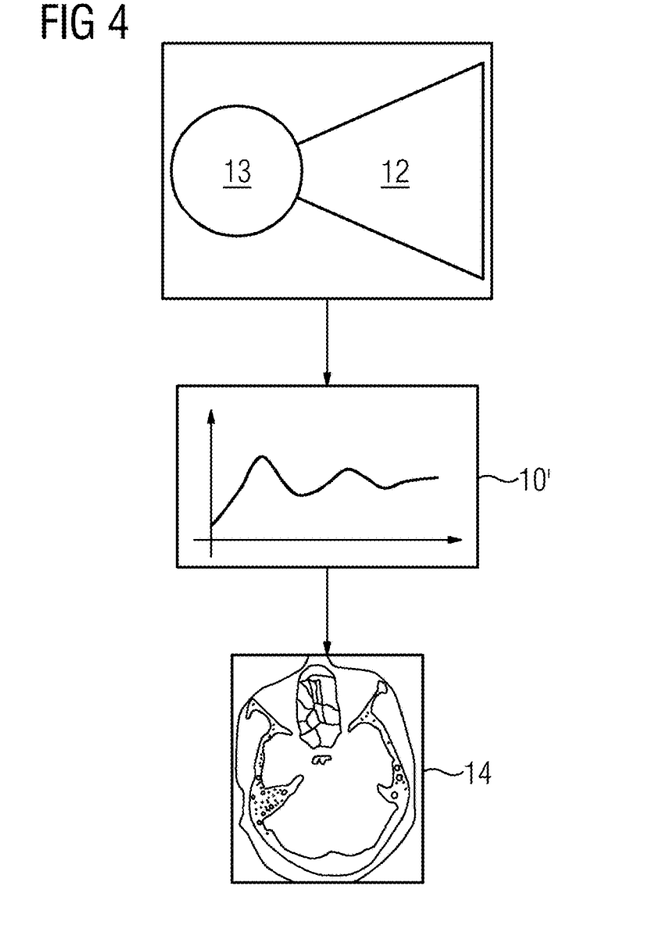
FIG. 4 depicts a schematic flow diagram of a further example of an embodiment of a method for creation of a movement-compensated image reconstruction.

The apparatus 1 is, for example, configured to carry out a method for x-ray based imaging. The x-ray imaging modality 2 creates a plurality of projection images of the object 6, for example in accordance with a known protocol for CBCT. For example, around 500 projection images of the object 6 may be created. A method for creation of a movement-compensated image reconstruction 14 is carried out. A schematic flow diagram of such a method is shown in FIG. 4.

For example in this case an optimal object movement trajectory 10' for the object 6 is created by application of the trained algorithm 12 to an optimal latent vector in the latent space 13 and the movement-compensated image reconstruction 14 is created depending on the plurality of projection images, with the assumption that the object 6 would have moved while the imaging method was being carried out, i.e. during the creation of the projection images, in accordance with the optimal object movement trajectory 10'.

The optimal latent vector is determined in this case by a predetermined cost function being minimized using the latent vector as the optimization parameter. A current object movement trajectory is determined for each optimization step with a current latent vector by application of the trained algorithm 12 to the current latent vector. A current image reconstruction is created depending on the plurality of projection images. This is undertaken, with the assumption that the object 6 would have moved in accordance with the current object movement trajectory while the imaging method was being carried out. A current value of the cost function is computed depending on the current image reconstruction.

As an alternative the current value of the cost function may be computed depending on a predetermined set of consistency conditions relating to the plurality of projection images, so that a current image reconstruction does not have to be created in the individual optimization steps.

Figure 3:
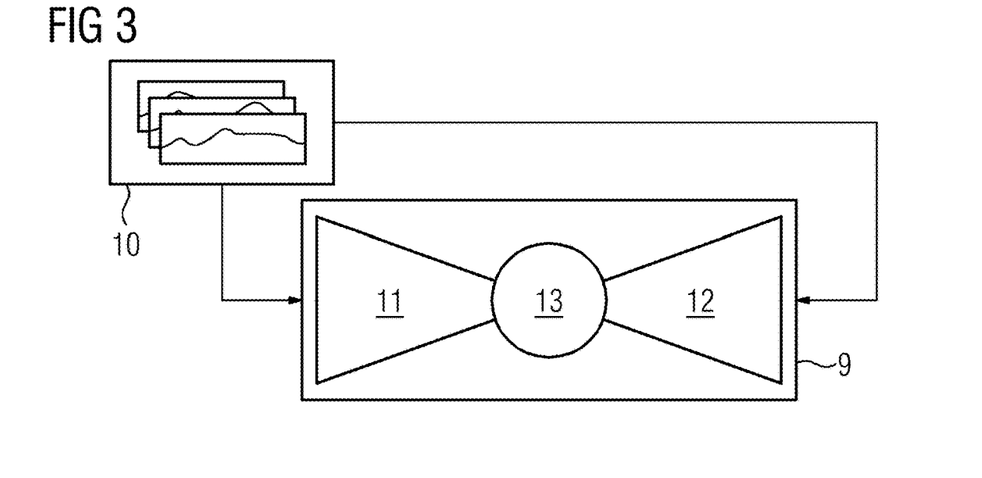
FIG. 3 depicts a schematic diagram of a training phase for training of an algorithm for carrying out an example of an embodiment of a method for creation of a movement-compensated image reconstruction.

The trained algorithm 12 may for example involve a decoder module 12 of an autoencoder 9, as is shown schematically in FIG. 3. During the training phase the autoencoder 9 has an encoder module 11, that may encode a training object movement trajectory 10 in a corresponding latent vector of the latent space 13. The decoder module 12 reconstructs the training object movement trajectory 10 based on the respective latent vector.

Figure 2:
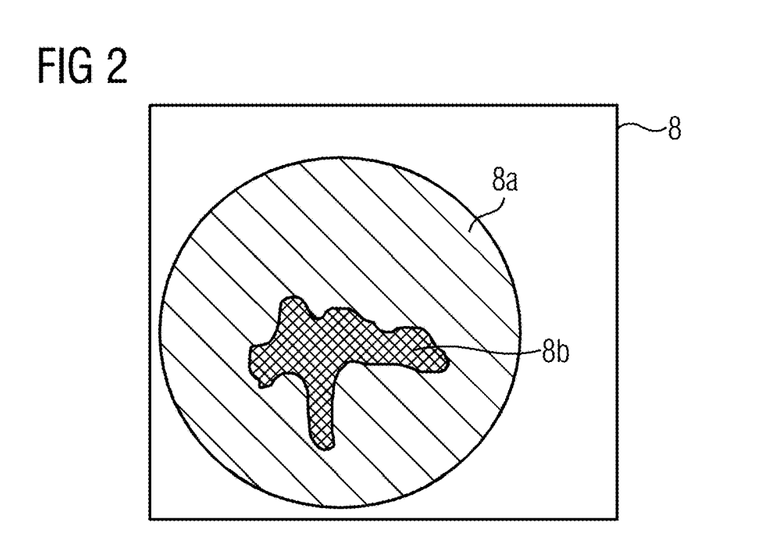
FIG. 2 depicts a schematic diagram of different parameter spaces for parameterization of object movement trajectories according to an embodiment.

The model of a fixed movement without any restriction is based on rotations and translation, typically defined as the specific Euclidian group in three dimensions SE(3). This movement model is very powerful, however most of the movement constellations that may be described by SE(3) are not realistic. The movements that may principally be described by rotations and translation, are shown schematically in FIG. 2 as square 8. A diversity of the possible movements is for example shown schematically in FIG. 2 as the square 8.

The sampling of the movement via spline nodes already reduces the quantity of the possible unrealistic movement constellations. The movements that may principally be described by splines are shown schematically in FIG. 2 as circle 8a, for example as a sub diversity of the diversity of all possible movements. Despite this, many unrealistic movement constellations are still possible. With patients who are lying on a table and are restricted by the human anatomy, only a subset of SE(3) is physically possible. This portion is shown schematically in FIG. 2 as irregular region 8b and represents the subset of SE(3) that only contains physically or anatomically possible movement constellations, for example as a smaller sub diversity of the movements able to be described by splines.

In various forms of embodiments, in a first step, movement trajectories of real patients are sampled as test object movement trajectories 10. This may be performed by tracking for example. A patient bears markers on their head for example, and a camera system tracks these markers. With the aid of the markers and the camera system a movement trajectory of the patient may be computed. Through the recording of, for example, several patients over several hours a very large database is produced with realistic test object movement trajectories 10.

Based on a set of realistic test object movement trajectories 10, the autoencoder 9 may be used for encoding and decoding of these test object movement trajectories 10. The autoencoder 9 may be configured as a regular autoencoder or as a variational autoencoder 9. An autoencoder 9 is for example defined by reproducing the input of the network in the output layer. Through the introduction of a constriction in the middle of the network, i.e., after the encoder module 11, the autoencoder 9 is forced to learn the latent space 13 of the test object movement trajectories 10 instead of carrying out a simple identity mapping.

The encoder module 11 may be an implicit neural network, for example in accordance with a SIREN architecture, as described in the publication by V. Sitzmann, J. Martel, A. Bergman, A. Lindell, G. Wetzstein: "Implicit neural representations with periodic activation functions", Advances in Neural Information Processing Systems. 2020; 33:7462-73. An advantage of the SIREN architecture is its capability of computing higher-order derivations. This is possible because the classical ReLu activation function is replaced by a sine function. As a result, a Jacobian regularization or a bending regularization, that forces a smooth and realistic mapping of latent space to the output space, so that for example small changes in the latent space 13 lead to small changes in the output space. It should be borne in mind that this type of behavior is also forced by the variation autoencoder 9. This characteristic may be important when the latent space 13 is used as parameterization for the movement compensation.

After successful training, the decoder module 12 of the autoencoder 9 may be extracted and used for the creation of the object movement trajectories.

A GAN may be used as an alternative to the autoencoder 9. In this case the input for the GAN would again be a latent vector, the generator module of the GAN maps a latent vector to an object movement trajectory and the loss is based on the distinction between true and so-called fake object movement trajectories.

After the training, the decoder module 12 may create a current object movement trajectory on the basis of the current latent vector. This object movement trajectory may then be translated into projection matrixes and used in the reconstruction algorithm in order to produce a current image reconstruction, that is based on the current object movement trajectory. By comparison with parameterization with splines however, only movement constellations result that are physically sensible.

The latent space 13 now represents the parameterization for the object movement trajectory. This means that the parameterization X is the latent vector. The movement compensation may then be defined in the regular notation by $$X' = \operatorname{argmin}_X c(r(I, X)),$$

or be defined by $$X' = \operatorname{argmin}_X c(I, X),$$

if the cost function c( ) is based on consistency conditions, for example epipolar consistency conditions. The solution to this minimization problem produces the optimal latent vector X', that resolves the movement compensation.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that the dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for creation of a movement-compensated image reconstruction for an x-ray based imaging method, the method comprising:
providing a plurality of projection images of an object using the x-ray based imaging method;
providing a trained algorithm that is trained to allocate an object movement trajectory to a latent vector of a latent space;
determining an optimal object movement trajectory by application of the trained algorithm to an optimal latent vector and wherein the movement-compensated image reconstruction is created depending on the plurality of projection images, wherein the object has moved in accordance with the optimal object movement trajectory while the x-ray based imaging method was carried out; and
determining the optimal latent vector by a cost function being minimized using the latent vector as an optimization parameter,
determining, for each optimization step with a current latent vector, a current object movement trajectory by application of the trained algorithm to the current latent vector; and
computing a current value of the cost function depending on the plurality of projection images, wherein the object has moved in accordance with the current object movement trajectory while the x-ray based imaging method was being carried out.

2. The method of claim 1, wherein the trained algorithm is configured to allocate a time series of rotations and translations in three-dimensional space to a latent vector of the latent space as an object movement trajectory.

3. The method of claim 2, wherein the plurality of projection images contains K projection images, wherein each projection image corresponds to one of K consecutive recording time spaces; and the time series contains K rotations and K translations.

4. The method of claim 1, wherein the trained algorithm is configured as a decoder module of an autoencoder or of a variational autoencoder.

5. The method of claim 4, wherein creating the trained algorithm comprises:

creating a plurality of training object movement trajectories that each describe an actual movement of a test object; and
for each of the training object movement trajectories:
creating a training vector in the latent space by an encoder module of the autoencoder or the variational autoencoder being applied to the respective training object movement trajectory;
creating a reconstructed object movement trajectory by the decoder module based on the training vector;
evaluating a loss function based on a deviation of the reconstructed object movement trajectory from the training object movement trajectory; and
adapting network parameters of the autoencoder or variational autoencoder depending on a result of the evaluation of the loss function.

6. The method of claim 1, wherein the trained algorithm is configured as a generator module of a GAN network.

7. The method of claim 6, wherein creating the trained algorithm comprises:
creating a plurality of training object movement that each describe an actual movement of a test object;
creating, by an artificial neural network configured as an encoder being applied to the respective training object movement trajectory, for each of the training object movement trajectories a training vector in the latent space; and
training the generator module and a discriminator module of the GAN network using the training vectors as input data.

8. The method of claim 7, wherein for each of the training object movement trajectories, for creation of the respective training object movement trajectory, the test object is monitored during a corresponding test period by at least one camera and the respective training object movement trajectory is determined based on camera images created by the at least one camera during the monitoring.

9. The method of claim 8, wherein at least one visual marker is attached to the test object and the respective training object movement trajectory is determined based on corresponding positions of the at least one visual marker in the camera images.

10. The method of claim 1, wherein, for each of the optimization steps, the method further comprises:
creating a current image reconstruction based on the plurality of projection images, wherein the object moves in accordance with the current object movement trajectory while the x-ray based imaging method was being carried out, and the current value of the cost function is computed depending on the current image reconstruction; or
computing the current value of the cost function based on a predetermined set of consistency conditions relating to the plurality of projection images.

11. The method of claim 1, wherein the x-ray based imaging method is a cone-beam computed tomography method.

12. An apparatus for x-ray based imaging, the apparatus comprising:
an x-ray imaging modality that is configured to create a plurality of projection images of an object;
a memory device that stores a trained algorithm that is trained to allocate an object movement trajectory to a latent vector of a latent space; and
at least one processing unit that is configured to:
determine an optimal object movement trajectory by application of the trained algorithm to an optimal latent vector and to create a movement-compensated image reconstruction depending on the plurality of projection images, wherein the object moves in accordance with the optimal object movement trajectory while imaging is being carried out; and minimize a cost function using the latent vector as an optimization parameter, in order to determine the optimal latent vector and, in doing so, to determine a current object movement trajectory for each optimization step with a current latent vector by application of the trained algorithm to the current latent vector, and to compute a current value of the cost function depending on the plurality of projection images.

13. The apparatus of claim 12, wherein the trained algorithm is configured to allocate a time series of rotations and translations in three-dimensional space to a latent vector of the latent space as an object movement trajectory.

14. The apparatus of claim 13, wherein the plurality of projection images contains K projection images, wherein each projection image corresponds to one of K consecutive recording time spaces; and the time series contains K rotations and K translations.

15. The apparatus of claim 12, wherein the trained algorithm is configured as a decoder module of an autoencoder or of a variational autoencoder.

16. The apparatus of claim 15, wherein creating the trained algorithm comprises:
creating a plurality of training object movement trajectories that each describe an actual movement of a test object; and
for each of the training object movement trajectories:
creating a training vector in the latent space by an encoder module of the autoencoder or the variational autoencoder being applied to the respective training object movement trajectory;
creating a reconstructed object movement trajectory by the decoder module based on the training vector;
evaluating a loss function based on a deviation of the reconstructed object movement trajectory from the training object movement trajectory; and
adapting network parameters of the autoencoder or variational autoencoder depending on a result of the evaluation of the loss function.

17. The apparatus of claim 12, wherein the trained algorithm is configured as a generator module of a GAN network.

18. The apparatus of claim 17, wherein creating the trained algorithm comprises:

creating a plurality of training object movement that each describe an actual movement of a test object;
creating, by an artificial neural network configured as an encoder being applied to the respective training object movement trajectory, for each of the training object movement trajectories a training vector in the latent space; and
training the generator module and a discriminator module of the GAN network using the training vectors as input data.

19. The apparatus of claim 18, wherein for each of the training object movement trajectories, for creation of the respective training object movement trajectory, the test object is monitored during a corresponding test period by at least one camera and the respective training object movement trajectory is determined based on camera images created by the at least one camera during the monitoring.

20. A non-transitory computer implemented storage medium that stores machine-readable instructions executable by at least one processor for creation of a movement-compensated image reconstruction for an x-ray based imaging method, the machine-readable instructions comprising:
providing a plurality of projection images of an object using the x-ray based imaging method;
providing a trained algorithm that is trained to allocate an object movement trajectory to a latent vector of a predetermined latent space;
determining an optimal object movement trajectory by application of the trained algorithm to an optimal latent vector and wherein the movement-compensated image reconstruction is created depending on the plurality of projection images, wherein the object has moved in accordance with the optimal object movement trajectory while the x-ray based imaging method was carried out; and
determining the optimal latent vector by a cost function being minimized using the latent vector as an optimization parameter,
determining, for each optimization step with a current latent vector, a current object movement trajectory by application of the trained algorithm to the current latent vector; and
computing a current value of the cost function depending on the plurality of projection images, wherein the object has moved in accordance with the current object movement trajectory while the x-ray based imaging method was being carried out.

* * * * *